US008003403B1

(12) United States Patent (10) Patent No.: US 8,003,403 B1
Levitsky (45) Date of Patent: Aug. 23, 2011

(54) OPTOCHEMICAL SENSORS FOR THE DETECTION OF LOW PRESSURE VAPORS BASED ON POROUS SEMICONDUCTORS AND EMISSIVE ORGANICS

(75) Inventor: Igor A. Levitsky, Fall River, MA (US)

(73) Assignee: Emitech, Inc, Fall River, MA (US)

( * ) Notice: Subject to any disclaimer, the term of this patent is extended or adjusted under 35 U.S.C. 154(b) by 430 days.

(21) Appl. No.: 12/051,233

(22) Filed: Mar. 19, 2008

(51) Int. Cl.
*G01N 21/76* (2006.01)
(52) U.S. Cl. ........ 436/172; 435/7.1; 435/174; 422/68.1; 422/82.05; 73/31.07; 73/863.71; 73/863.81
(58) Field of Classification Search .................. None
See application file for complete search history.

(56) References Cited

U.S. PATENT DOCUMENTS

| 5,338,415 A | 8/1994 | Sailor et al. |
| 5,453,624 A | 9/1995 | Sailor et al. |
| 6,720,177 B2 | 4/2004 | Ghadiri et al. |
| 6,780,649 B2 | 8/2004 | Armstrong et al. |
| 7,209,122 B2 | 4/2007 | Oguro |
| 7,226,733 B2 | 6/2007 | Chan et al. |

OTHER PUBLICATIONS

Weaver, M.S. et al. Recent progress in polymers for electroluminescence: microcavity devices and electron transport polymers, 1996, Thin Solid Films, vol. 273, pp. 39-47.*
Chan, S. et al., Nanoscale microcavities for biomedical sensor applications, 2000, Porceedings of SPIE, vol. 3912, pp. 23-34.*
I. A. Levitsky et al., "Fluorescent Polymer-Porous Silicon Microcavity Devices for Explosive Detections", Applied Physics Letters 90, 041904 (2007).
L.T. Canham, "Silicon Quantum Wire Array Fabrication by Electrochemical and Chemical Dissolution of Wafers," Appl. Phys. Lett. vol. 57, No. 10, Sep. 3, 1990, pp. 1046-1048.
Keith J. Albert et al., "Cross-Reactive Chemical Sensor Arrays," Chemical Reviews, 2000, vol. 100, No. 7, pp. 2595-2626.
Jay W. Grate, "Acoustic Wave Microsensor Arrays for Vapor Sensing," Chemical Reviews 2000, vol. 100, No. 7, pp. 2627-2647.
Selena Chan et al., "Identification of Gram Negative Bacteria Using Nanoscale Silicon Microcavities," J. Am. Chem. Soc. 2001, vol. 123, No. 47, pp. 11797-11798.
Andreas Janshoff et al., "Macroporous p-Type Silicon Fabry-Perot Layers. Fabrication, Characterization, and Applications in Biosensing," J. Am. Chem. Soc. 1998, vol. 120, No. 46, pp. 12108-12116.
Victor S.-Y. Lin et al., "A Porous Silicon-Based Optical Interferometric Biosensor," Science vol. 278, Oct. 31, 1997, pp. 840-843.
Jye-Shane Yang et al., "Flourescent Porous Polymer Films at TNT Chemosensors: Electronic and Structural Effects," J. Am. Chem. Soc. 1998, vol. 120, No. 46, pp. 11864-11873.

\* cited by examiner

*Primary Examiner* — Yelena G Gakh
*Assistant Examiner* — Robert Xu

(57) ABSTRACT

A chemical sensor for detecting organic or inorganic target vapors and comprising a silicon member having a silicon surface with semiconductor pores therein, at least one luminescent sensory material entrapped in the semiconductor pores. The luminescent spectral material is exposed to the target vapors, wherein an excitation of the at least one luminescent sensory material results in a luminescent spectral response due to emission interference. The change in the luminescent spectral response is measured during this exposure.

19 Claims, 6 Drawing Sheets

OPTOCHEMICAL SENSORS FOR THE DETECTION OF LOW PRESSURE VAPORS BASED ON POROUS SEMICONDUCTORS AND EMISSIVE ORGANICS

STATEMENT REGARDING FEDERALLY SPONSORED RESEARCH OR DEVELOPMENT

This invention was made with Government support under US Army No. W56 HZV-07-C-0150. The Government may have certain rights in the invention.

FIELD OF THE INVENTION

The present invention relates to a novel method for the precise detection of gases with a low level of saturated vapor pressure. This method discloses the fabrication and application of new optochemical sensors based on composites of emissive sensory organics and porous semiconductors.

BACKGROUND OF THE INVENTION

The research and development of new MEMS technologies and electronic materials for the detection of toxic and explosive vapors, with high sensitivity and selectivity is of utmost importance for many commercial, environmental, security applications and for US military missions.

Detection techniques include a variety of physical and chemical methods related to changing the output signal under exposure to target analytes. Physical methods include: nuclear quadrupole resonance, ion mass spectroscopy, gas chromatography, X-ray diffraction, electron capture detection, and laser photofragmentation. These techniques are selective enough, but can be expensive, bulky and cannot be employed for real-time, fast and remote analyte detection. Also, most of the chemical sensors have been studied, developed, and fabricated in the macro format using traditional techniques for the deposition of sensory polymers (spin-casting, coating, spraying) onto relatively large area substrates followed by coupling to a separated detection/acquisition system (Walt et al, Chem. Rev. 100: 2595, 2000; Grate, Chem. Rev. 100: 2627, 2000). Such devices could be employed for pattern recognition of vapor mixtures. However, vapor concentration should be high enough to prevent a false response and to correctly identify the explosive chemical signature. Since many toxic and explosive vapors (for example, TNT, RDX, PETN) are related to low pressure vapors, the critical issue becomes an enhancement of sensor sensitivity and selectivity to provide a fast, real-time response with a minimum false alarm.

Porous silicon (PSi) has been extensively studied for a number of semiconductor applications since it was discovered in the late 1950's. More recently, PSi has been shown to exhibit visible luminescence (Canham, Appl. Phys. Lett. 57:1046; 1990), suggesting promising applications in silicon-based optoelectronic devices. Other porous semiconductor materials such as gallium arsenide, for example, have also been studied to a lesser extent (Schmuki et al, Appl. Phys. Lett. 72:1039; 1998).

U.S. Pat. Nos. 5,338,415; 5,453,624; and 6,720,177 (Sailor et al) describe a method for the detection of chemicals by reversible quenching of PSi photoluminescence and a device for the detection of organic solvents by PSi photoluminescence, respectively. A silicon wafer was electrochemically etched (anodization) with a 50:50 ethanol/hydrofluoric acid (HF) solution to produce a PSi wafer. When the PSi wafer was illuminated with a laser light source in the presence of an organic compound, such as tetrahydrofuran (THF), diethyl ether, methylene chloride ($MeCl_2$), toluene, o-xylene, ethanol and methanol (MeOH), the inherent luminescent emission intensity of the PSi was significantly decreased (i.e., the photoluminescent response of the PSi was quenched). In these patents it is noted that the transduction mechanism in the above patents is the luminescence caused by porous Si only.

Lin et al. describe a biosensor based on induced wavelength shifts in the Fabry-Perot fringes in the visible light reflection spectrum of a thin flat film of PSi (Science 278:840; Oct. 31, 1997). Optically flat thin films of PSi, prepared by electrochemical etching are sufficiently transparent to display Fabry-Perot fringes in their optical reflection spectrum. A recognition element is immobilized on the flat PSi film. Subsequent binding of an analyte to the recognition element therefore results in a change in the refractive index of the PSi film and is detected as a corresponding shift in the interference pattern. Janshoff et al (J. Am. Chem. Soc. 120:12108; 1998) also describe the PSi for biosensor applications utilizing a shift in a Fabry-Perot fringe pattern, created by multiple reflections of illuminated white light on the air/PSi layer and PSi/bulk silicon interface, as a means for detecting molecular interactions of species in a solution with immobilized ligands as receptors.

U.S. Pat. No. 6,780,649 (Armstrong et al) describes the PSi layer modified with recognition elements. A PSi layer has its own photoluminescence (PL). A PSi modified with such recognition elements can interact with a target analyte so that a wavelength shift and/or change in PL intensity. Thus, transduction mechanism in these sensors is photoluminescence of PSi, but not of the sensory element itself.

U.S. Pat. No. 7,226,733 (Fauchet et al) describes a biological sensor comprising of a porous semiconductor structure including strata of alternating porosity; and one or more probes coupled to the porous semiconductor structure. The probes that are binding to a target molecule result in change in a refractive index of the biological sensor upon binding of more probes to the target molecule. This description also includes an emission pattern which shifts following exposing, whereby a shifted photoluminescent emission pattern indicates the presence of the target molecule in the sample. However, this invention is related to only the microcavity biosensors "which are useful for identifying the presence of a biological target molecule or organism in a sample, as well as methods for making such microcavity biosensors and their use". In addition, as it follows from the detailed description, emission of the sensors comes only from the porous Si, but not from the organic sensory material entrapped inside PSi pores The series of articles and patents by Swager et al (J. Am. Chem. Soc. 120: 11864, 1998; U.S. Pat. No. 7,208,122) propose a new concept, namely the "molecular wire" approach, related to emissive optochemical sensors for the detection of explosive vapors. The major issue here is the amplification mechanism based on an energy migration effect allowing very high device sensitivity, which is of utmost importance for the detection of explosives with a low pressure of saturated vapors. U.S. Pat. No. 6,686,206 and an article (J. Phys. Chem. B 106:8468, 2001) by Levitsky et al also describes the optochemical sensors involving amplification mechanism of luminescence, however, based on the direct Forster energy transfer. Despite high sensitivity, the above emissive sensors suffer low selectivity as quenching or enhancing of the emission demonstrates the similar behavior for different parts of the luminescent spectrum.

It would therefore be desirable to have material useful for detecting low pressure vapors, which combines the high sensitivity of the emissive sensory elements and dependence of the refractive index of the porous semiconductor on target molecules.

SUMMARY OF THE INVENTION

The present invention provides an approach for the development of optochemical sensors/sensor array for the detection of explosives and toxic compounds with low pressure of saturated vapors.

In this invention, the sensory part of the device is comprised of a nanoporous semiconductor (monolayer or micro cavity), pore size of 2-500 nm, coupled with organic transducers (sensory material such as sensory emissive polymers, sensory dyes or quantum dots or sensory non-emissive polymers blended with dyes or quantum dots) which are specific to target vapors. For porous monolayer the luminescence of sensory organic will be patterned by Fabry-Perot fringes. In the microcavity case, the broad luminescence band of the emissive organic will be patterned by a narrow "hole" or peak as a result of the light interference in the photonic crystal. The binding of target molecules with the sensory emissive organic affects the pholuminescent (PL) spectrum by two ways: changing the total PL intensity (quenching/enhancement) and shifting the spectral position of the "hole"/peak (or Fabry-Perrot fringes) as a result of the refractive index change due to molecular sorption inside photonic crystal. Then the PL time trace upon analyte exposure at different wavelengths should be different in the vicinity of the spectral "hole" or peak. In the following we will consider the response of microcavity based sensor only, as it demonstrates more pronounced effect as compared with Fabry-Perot fringes. However, the principles of the present invention are considered as covering both microcavity and Fabry-Perot types.

More particularly there is provided a chemical sensor for detecting organic or inorganic target vapors and comprising a semiconductor substrate having a surface with semiconductor pores therein, at least one luminescent sensory material entrapped in the semiconductor pores, means for exposing the luminescent spectral material to the target vapors, wherein an excitation of said at least one luminescent sensory material results in a luminescent spectral profile due to emission interference, and means for measuring the change in the luminescent spectral profile during said exposure.

In accordance with other aspects of the present invention, per one or more of the following features, the intensity of the luminescence is monitored on a real-time basis as time traces during the vapor exposure at least two different wavelengths of the luminescent spectral profile; including monitoring the time traces of the luminescent intensity as relates to at least one factor affecting luminescent spectral profile including the spectral shift due to a change of the refractive index upon vapor exposure; including monitoring the time traces of the luminescent intensity as relates to at least one factor affecting luminescent spectral profile including luminescence quenching or enhancing due to specificity (selective binding) of target vapors to luminescent sensory material; wherein the luminescent spectral profile is caused by the emission of the sensory material only, due to multiple light reflection and interference inside the semiconductor pores; wherein the luminescent spectral profile is caused by Fabry-Perot fringes of porous monolayer or narrow peak of microcavity fabricated by multiple layers of alternating porosity; wherein the luminescent spectral profile induces a significant narrowing of the broad luminescence bandwidth of the luminescent sensory material entrapped in the semiconductor pores; wherein the luminescent spectral profile appears as a narrow spectral hole in the broad luminescence bandwidth of the luminescent sensory material entrapped in the semiconductor pores; wherein said luminescent sensory material entrapped in the semiconductor pores is selected from emissive sensory polymers; emissive sensory molecules or quantum dots; organic emissive molecules or quantum dots blended with non-emissive sensory polymers; wherein said semiconductor pores have size in the range of 2-500 nm and made in semiconductor bulk material to provide the light interference for reflected and emissive light; wherein porous microcavity or porous monolayer are situated on a top of the bulk semiconductor material and from which they are fabricated; wherein porous microcavity or porous monolayer are prepared as a free standing membrane; wherein the semiconductor is selected from the group consisting of Group II/VI semiconductors, Group III/V semiconductors and Group IV semiconductors; wherein the semiconductor is selected from the group consisting of Cds, CdSe, InP, GaAs, Ge, Si and doped Si; and which provides an enhanced selectivity over the sensor comprising the same luminescent sensory material deposited onto a flat substrate and do not possessing the luminescent spectral structure because of multiple intensity monitoring at different detecting wavelengths.

Also, in accordance with the present invention there is provided a method of detecting a target vapor employing at least one luminescent sensory material entrapped in semiconductor pores, comprising the steps of:

excitation said at least one luminescent sensory material resulting in a luminescent interference profile;

exposing the luminescent interference profile to the target vapor;

and measuring the change of the luminescent interference profile during such exposure.

In accordance with still other aspects of the present invention, per one or more of the following features, the step of measuring the luminescent interference profile includes measuring the change of the luminescent intensity at least at two different wavelengths from the luminescent interference profile; said luminescent interference profile is caused by the emission of the sensory material only; the luminescent profile is selected from one of Fabry-Perot fringes of a porous monolayer or the resonance peak of microcavity fabricated by multiple layers of alternative porosity; the step of measuring relies on, not only a spectral shift of the photoluminescence spectral profile, but also from a simultaneous change of the photoluminescence intensity as a result of the binding of target molecules to luminescent sensory material entrapped inside the semiconductor pores; the step of measuring includes real-time monitoring of the emission intensity at different wavelengths selected from the photoluminescence spectral profile upon analyte exposure; the intensity of the luminescence is concurrently monitored on a real-time basis as time traces during the vapor exposure at least two different wavelengths of the luminescent spectral profile, including monitoring the time traces of the luminescent intensity as relates to at least one factor affecting luminescent spectral profile including the spectral shift due to a change of the refractive index upon vapor exposure, and including monitoring the time traces of the luminescent intensity as relates to at least one factor affecting luminescent spectral profile including luminescence quenching or enhancing due to specificity (selective binding) of target vapors to luminescent sensory material; the luminescent spectral profile is caused by the emission of the sensory material only, due to multiple light reflection and interference inside the semiconductor pores; the luminescent profile is caused by Fabry-Perot fringes of porous monolayer or narrow peak of micro-cavity fabricated by multiple layers of alternating porosity; the luminescent spectral profile induces a significant narrowing of the broad luminescence bandwidth of the luminescent sensory material entrapped in the semiconductor pores in the case of the microcavity; the luminescent spectral profile appears as a narrow spectral hole in the broad luminescence bandwidth of the luminescent sensory material entrapped in the semiconductor pores; and the luminescent sensory material entrapped in the semiconductor pores is selected from emissive sensory polymers; emissive sensory molecules or quantum dots; organic emissive molecules or quantum dots blended with non-emissive sensory polymers.

DETAILED DESCRIPTION

Figure 1:
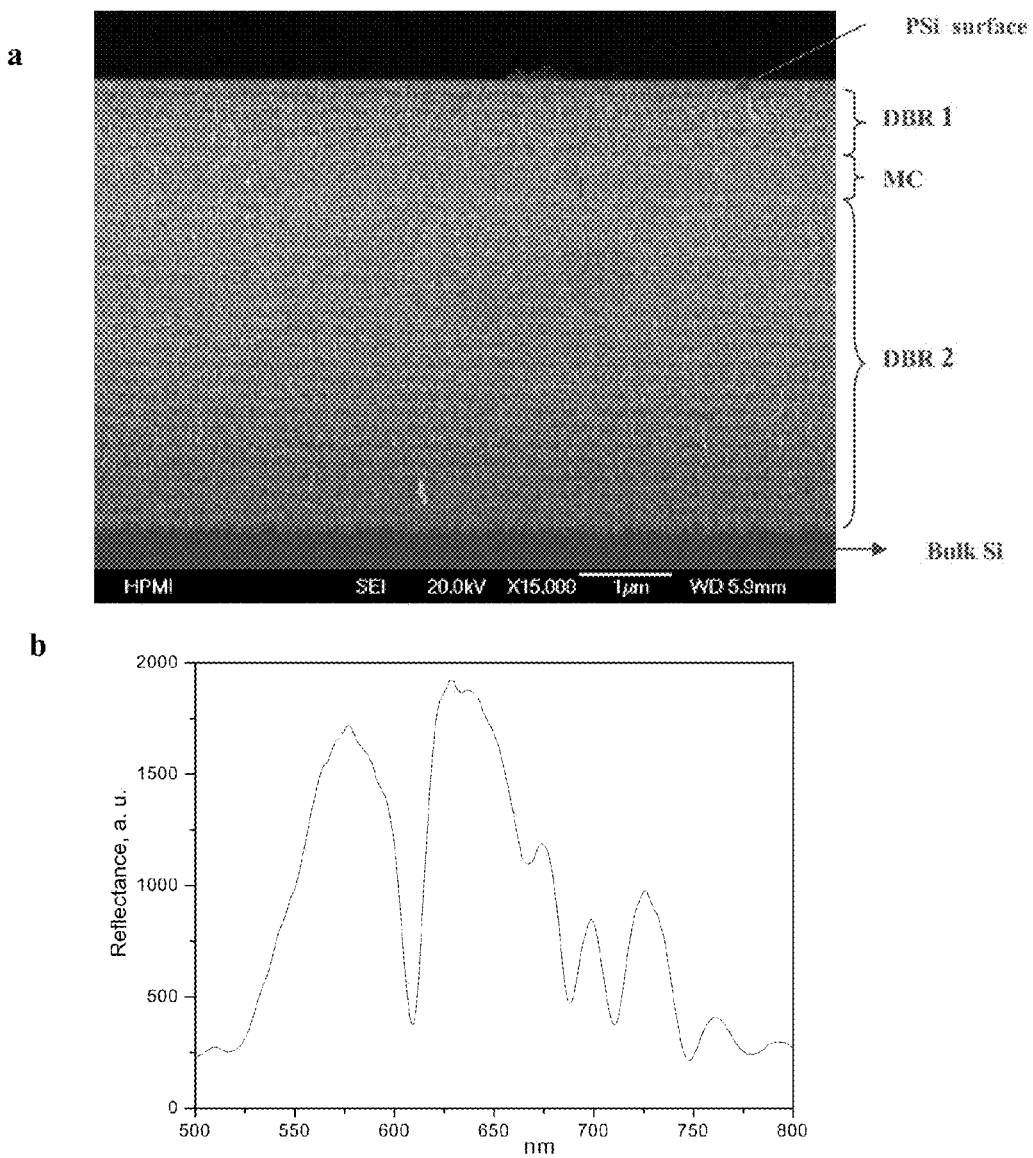
FIG. 1(a) Cross-sectional SEM image of a DBR1/MC/DBR2 structure. First distributed Bragg reflector (DBR1) and second DBR2 contains 5 and 20 periods of porous silicon multilayers of high and low porosity. The 200 nm thick MC layer is between DBR1 and DBR2.
FIG. 1(b): Experimental reflectivity spectra of a DBR 1/MC/DBR 2 tuned to 608 nm.

The use of a PSi microcavity for chemical sensing is not new and optical sensors based on luminescence/reflectance in microcavity have been already reported (see references in the "background of invention" section). Microcavity (MC) resonator (interference optical filter or 1D photonic crystal which is composed of alternating silicon layers with high and low porosity is attractive for optical sensing due to sharp peak/peaks (FWHM ~10 nm) in the visible/NIR spectral range [see refs. in the introduction]. Actual MC resonator consists of the first DBR 1, microcavity itself, and second DBR2 (FIG. 1a). In the following DBR1/MC/DBR2 structure we will call for simplicity sake as a microcavity (MC). It was several reports about PSi MC based sensors where non-emissive sensory material was entrapped into porous structure and spectral shift of PSi luminescence peak upon analyte exposure has been used as a transduction mechanism [see Fauchet's pat., Armstrong's pat. and Fauchet, et al, J. Am. Chem. Soc. 123: 11797, 2001]. However these sensors were mostly employed for the detection of biomolecules from the liquid medium and could not be employed for the sensing of low pressure vapors when a high sensitivity is required.

On the other hand, chemical optical sensors based on specially designed sensory polymers specific to the target vapors blended with solvatochromic dyes (optical transducers) or polymers with their own luminescence have received much attention for the past years (see refs. to Swager's and Levitsky's papers in the "background of invention" section). Such sensors demonstrated high sensitivity (ppb range). Nevertheless, their selectivity suffers due to a lack of precision detection of the spectral shift and intensity change under analyte exposure because of the broad spectral band of the solvatochromic dyes or conjugated emissive polymers (FWHM ~100-150 nm).

Figure 7:
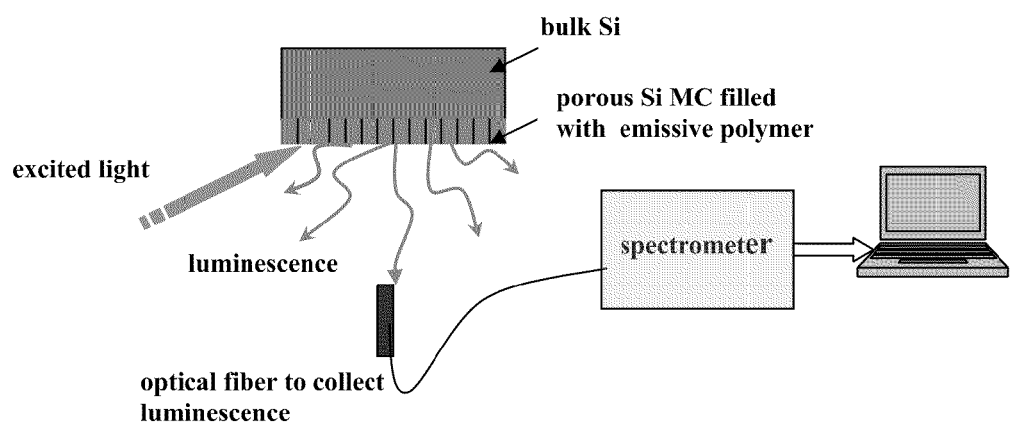
FIG. 7 is a schematic diagram of one embodiment of an apparatus used to detect photoluminescence.

In the presented invention, emissive sensory organics (in particular emissive conducting polymers) are coupled with MC to provide the not only high sensitivity (PL quenching), but also high selectivity as a result of change of the MC refractive index. Refer to FIG. 7 herein for a schematic diagram of one embodiment of an apparatus used to detect photoluminescence.

Figure 2:
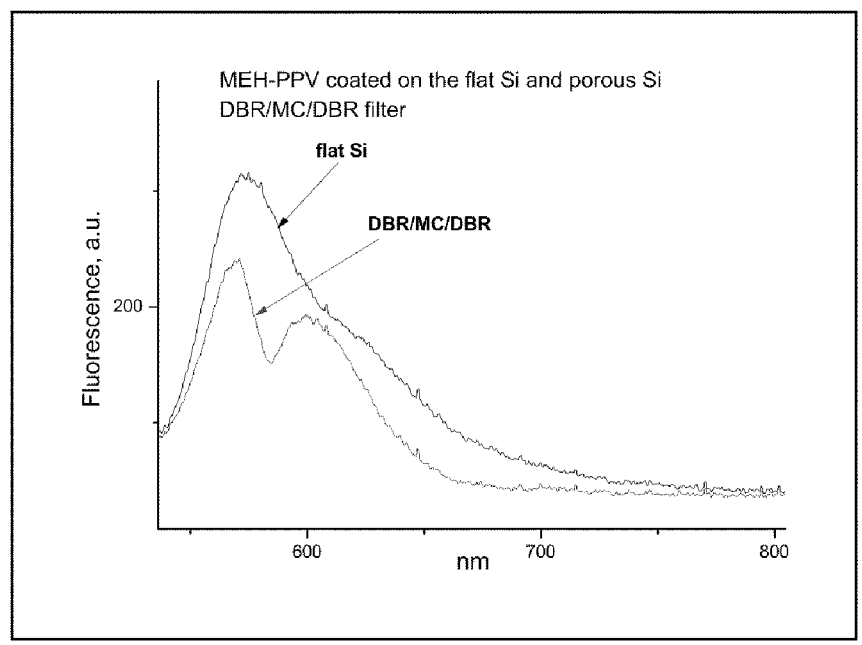
FIG. 2: Fluorescence of MEH-PPV spun cast on flat Si (black) and DBR1/MC/DBR2 structure (red) followed by heating and surface rinsing.

FIG. 2 shows the PL spectral profile of MEH-PPV (sensory polymer to TNT) coupled with microcavity. Coupling methods can include spin cast, coating, impregnation and vacuum filling.

The drop of the polymer PL at 585 nm (spectral "hole") indicates that the polymer is entrapped in near the surface area of the DBR/MC/DBR structure (FIG. 2). This surface-only entrapping means that the fluorescence emission at MC resonance peak wavelength is not reflected (as distinct from other wavelengths at stop-band) leading to the intensity reduction (I=585 nm) which is observed experimentally.

Figure 3:
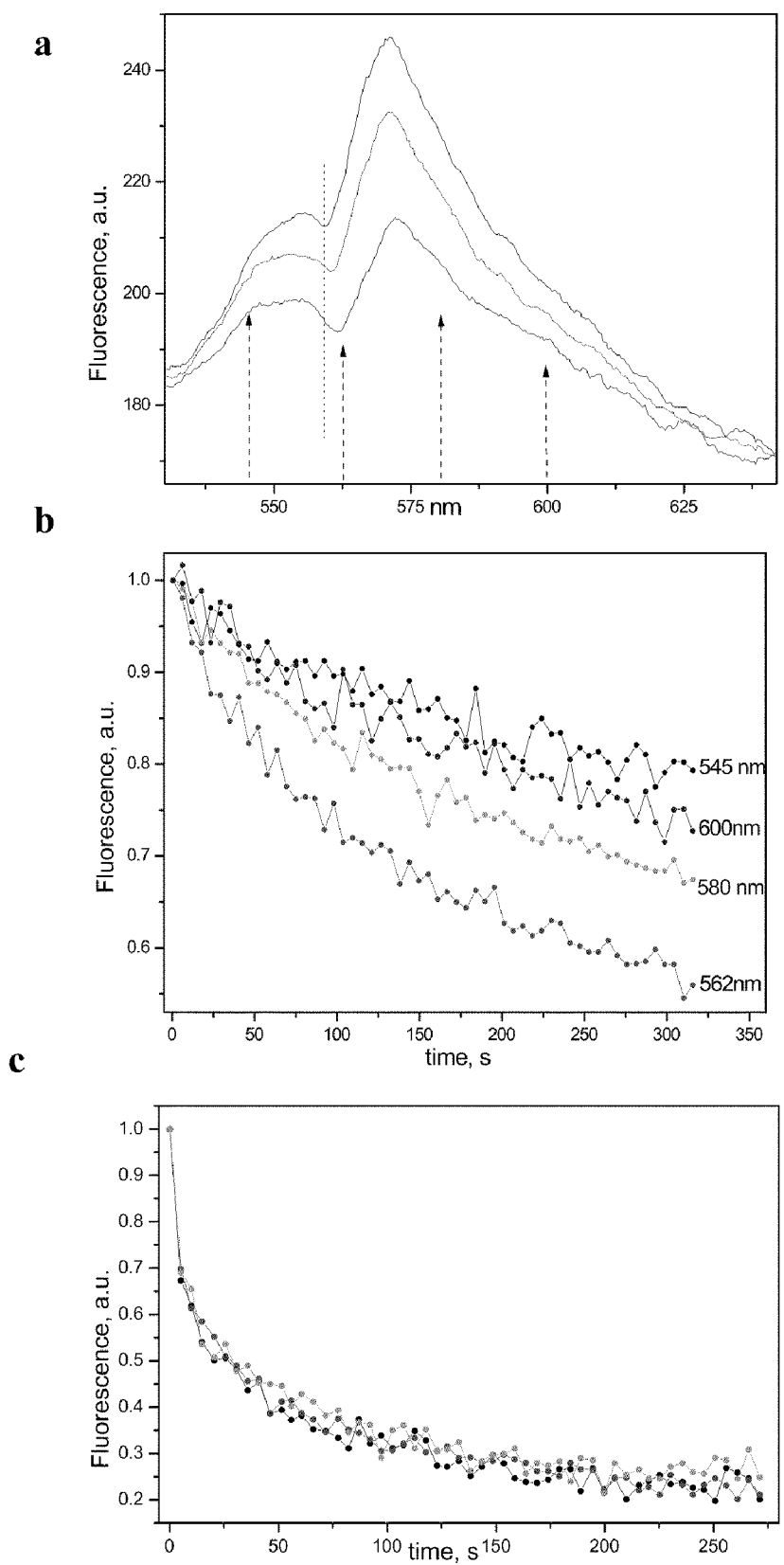
FIG. 3(a) Evolution of fluorescence of MEH-PPV entrapped into PSi MC under TNT vapors: black—initial, red—after 50 s, blue—after 250 s. Dotted black line corresponds to an initial spectral position of the MC "hole".
FIG. 3(b) time traces of the fluorescence for four detecting wavelengths (shown by arrows in FIG. 3a)
FIG. 3(c) time traces of the fluorescence for MEH-PPV spun cast onto flat Si (spectrum is shown in FIG. 2) for detecting wavelengths 550 nm (black), 570 nm (red) and 600 nm (green).

FIGS. 3a and 3b demonstrates PL quenching under TNT exposure for four different wavelengths and corresponding time scans. The highest PL quenching (~45% for 300 s) corresponds to the position of MC spectral "hole" (562 nm) which is a result of the "hole" spectral shift (~1 nm) toward the longer wavelengths (FIG. 3a). Thus, the time traces monitored at different detecting wavelengths provide the multiple data set which is specific for the nature of analyte molecule. Contrary for the same polymer spun cast on the flat Si substrate time traces are the same at different detecting wavelengths (FIG. 3c)

Freestanding MC thin membranes coupled with MEH-PPV also demonstrate the same trend under TNT exposure. However, thin membranes are very fragile and their filling should be done with precaution, making this process difficult for future technology development.

Figure 4:
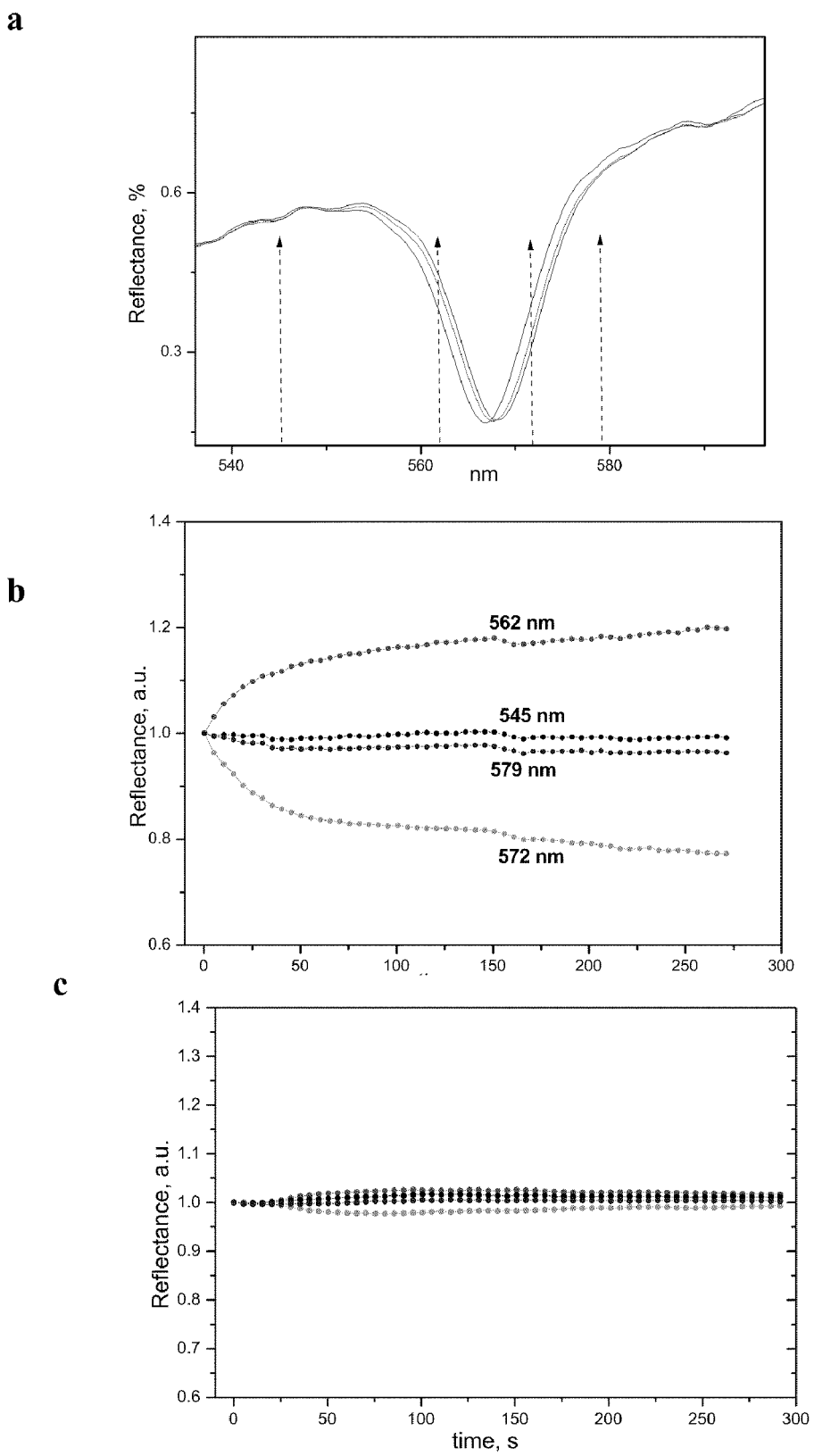
FIG. 4(a) Evolution of reflectance of PSi MC filled with MEH-PPV under TNT vapors: black—initial, red—after 50 s, blue—after 250 s.
FIG. 4(b) time traces of the reflectance for four wavelengths (shown by arrows in FIG. 3 a).
FIG. 4(c) time traces at same wavelengths under TNT vapors for PSi MC itself.

In addition to the fluorescence response, described sensors also demonstrate sensitivity to the target analyte in reflective mode. FIG. 4a-b demonstrates the red shift of MC peak in the reflectance spectra and corresponding time traces under exposure of saturated TNT vapors. For comparison, time traces of the same MC without entrapped MEH-PPV are shown in FIG. 4c, when no shift was detected. Thus, the entrapping of the sensory polymer inside MC allows the detection of analytes with low pressure of saturated vapors while the "empty" MC does not exhibit any response to the vapor exposure.

Figure 5:
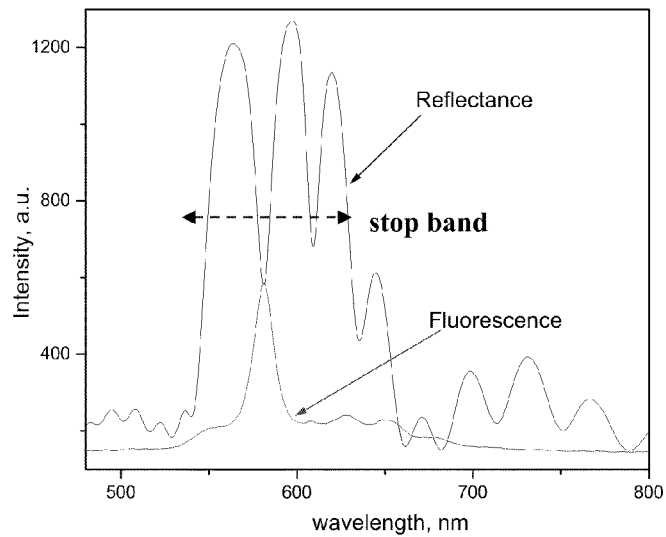
FIG. 5 Narrow PL peak of MEH-PPV polymer (red), which is infiltrated in the PSi MC. PL peak position matches with resonance MC peak of reflectance spectrum.

Another example shows a deep polymer infiltration into PSi MC as distinct from the near surface entrapping (FIG. 3), which also can be employed for the vapor detection. In this case a narrow PL peak (instead of spectral "hole" as for near surface entrapping) is observed due to photon confinement inside MC. A peak existence is an indication that polymer was infiltrated sufficiently deep and penetrated through the first DBR 1 reaching at least MC layer (FIG. 1a). Then an emission from MC will be suppressed in the spectral range of the stop band, which high reflectance dictates the PL scattering inside MC structure, except the narrow resonance peak possessing the low reflectance (FIG. 5). The confirmation of that is the matching of PL peak position with resonance peak of reflectance spectrum (FIG. 5).

Figure 6:
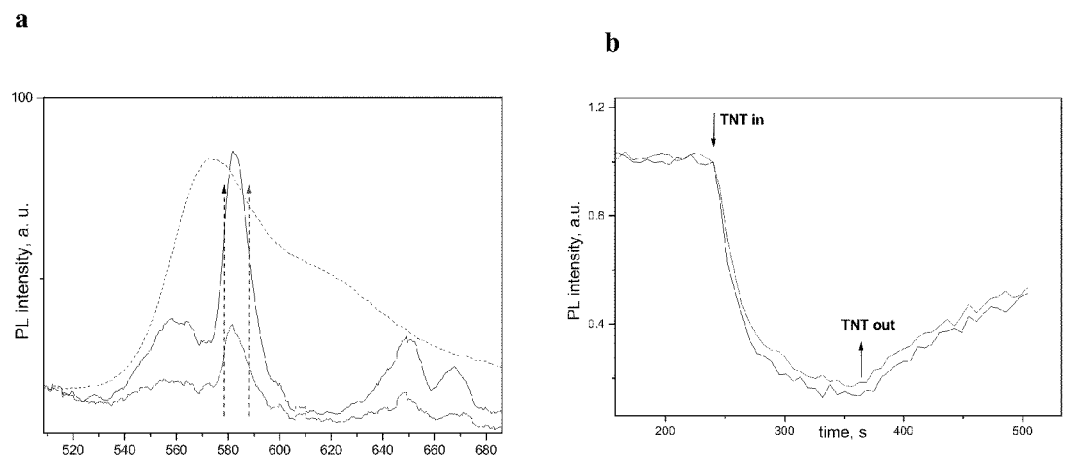
FIG. 6(a). Photoluminescence spectrum of microcavity infiltrated with MEH-PPV prior (black) and after 120 min exposure upon TNT (red) in the flat flow cell. Dash arrows show the detection wavelengths used for the time scan (FIG. 6b). Blue dashed spectrum is PL of MEH-PPV spun cast on the flat Si.
FIG. 6(b) PL time scans at two wavelengths determined from FIG. 5a. Small red shift is observed.

FIG. 6a demonstrates the PL quenching of MC deeply infiltrated with emissive sensory polymer upon exposure of TNT vapors. For comparison, a broad PL spectrum for polymer deposited on the flat substrate is presented (FIG. 6a, blue dashed line). Small PL bands at left and right sides from MC peak is a result of not full suppression of the polymer emission since spectral width of the stop band in the reflection (FIG. 5) is comparable with that of the broad PL band for polymer deposited on the flat substrate (FIG. 6a, blue dashed line). FIG. 6b shows time scans of the PL quenching upon TNT exposure for two detecting wavelengths (at the right and left shoulders of MC emissive peak). A slight shift of MC peak to the longer wavelengths (red shift) can be observed according to the difference between time scan for the left (black) and right (red) shoulders (FIG. 6b). The nature of the spectral shift is similar to that observed for polymer with near surface entrapping (FIG. 3): TNT vapors penetrate inside porous MC and induce the change of the refractive index leading to the spectral shift toward longer wavelengths.

Thus, in accordance with the present invention, unlike that described in the prior art, the transduction mechanism of the present invention employs a sensor technique that relies on not only a spectral shift of the PL spectral profile (pattern) but also from a simultaneous change of the PL intensity as a result of binding of target molecules to luminescent sensory material entrapped inside PSi pores.

Another principal distinction of the present invention is that the sensory material entrapped inside PSi pores is a luminescent material with quantum yield considerably higher than normal PSi luminescence. Previous related prior art disclosed as a transduction mechanism the PL spectral shift of PSi luminescence pattern, while sensory material was non-emissive. Also, the sensory material of the present invention does not require the special binders or/and Si surface functionalization to be bound to the inner walls of Si pores as it is described in the prior art. In addition, the method of detection of the present invention includes the real-time monitoring upon the analyte exposure of the emission intensity at different wavelengths selected from the PL spectral structure, but not comparison of the spectral position of the PL peak prior and after analyte exposure as it is presented in the prior art.

Finally, the present invention uses an approach that is distinctive from any emissive, chemosensors, where the sensory material is deposited onto a flat substrate resulting in the same PL time trace for different wavelengths (U.S. Pat. No. 7,208,122). Thus, even one sensory element coupled with porous photonic crystal can provide the manifold of responses specific to target molecules. It means that the present approach provides a simple and effective concept in the design of a novel sensor array for detection of explosive/toxic vapors.

Other advantages of the proposed detection system over existing optical chemosensors/sensor arrays can be formulated as follows:

Huge interface area of porous semiconductors ranges from 200 to 800 $m^2/cm^3$, which provides numerous sites between sorbent polymers and analyte vapors. That should dramatically increase sensitivity and dwelling time.

Possibility to fabricate porous microcavity (MC) as a free-standing membrane. Such a design should facilitate the membrane filling with polymers/dyes and of pumping the vapors.

Simple and cost effective fabrication process in the case of Si (electrochemical anodization of Si and MC impregnation/coating with the organics) that does not require high vacuum deposition, photolithography and clean room facilities.

Easy integration with other optoelectronic Si based modules making the sensory system autonomous, flexible and adaptive to various tasks according to MEMS requirements.

Thus, the presented invention provides for the fabrication of novel nanocomposite based optochemical sensors with superior sensing properties for fast, real-time, standoff detection explosive/toxic vapors.

What is claimed is:

1. A method of detecting a target vapor employing at least one luminescent sensory material entrapped in semiconductor porous structure, comprising the steps of: excitation said at least one luminescent sensory material resulting in a narrow luminescent peak;
   wherein the narrow luminescent peak is the result of sufficient or deep infiltration of sensory material inside the porous structure so that the sensory material fills at least 20% of the depth of the porous structure; wherein the bandwidth of the luminescent peak is in the range of 0.5-25 nm; exposing the luminescent sensory material to the target vapor; and measuring the change of the luminescent peak during such exposure.

2. The method of claim 1 wherein the step of measuring the luminescent peak includes measuring the change of the luminescent intensity at least at two different wavelengths from the luminescent peak.

3. The method of claim 2 wherein said luminescent peak is caused by the emission of the sensory material only.

4. The method of claim 1 wherein the luminescent peak is selected from one of Fabry-Perot fringes of a porous monolayer or the resonance peak of microcavity fabricated by multiple layers of alternating low and high porosity, wherein the first layer has porosity lower than 48% and the second layer has porosity higher than 55% to provide a sufficient or deep infiltration of sensory material inside porous microcavity.

5. The method of claim 1 wherein the step of measuring relies on, not only a spectral shift of the luminescent peak, but also from a simultaneous change of the luminescence intensity as a result of the binding of target molecules to luminescent sensory material entrapped inside the semiconductor pores.

6. The method of claim 1 wherein the step of measuring includes the real-time monitoring of the emission intensity upon the analyte exposure at different wavelengths selected from the luminescent peak.

7. The method of claim 1 wherein the intensity of the luminescence is concurrently monitored on a real-time basis as time traces during the vapor exposure at least at two different wavelengths of the luminescent peak.

8. The method of claim 7 including monitoring the time traces of the luminescent intensity as relates to at least one factor affecting luminescent peak including the spectral shift due to a change of the refractive index upon vapor exposure.

9. The method of claim 7 including monitoring the time traces of the luminescent intensity as relates to at least one factor affecting luminescent peak including luminescence quenching or enhancing due to specificity (selective binding) of target vapors to luminescent sensory material.

10. The method of claim 1 wherein the luminescent peak is caused by the emission of the sensory material only, due to multiple light reflection and interference inside the semiconductor pores.

11. The method of claim 1 wherein the luminescent peak is caused by Fabry-Perot fringes of porous monolayer or narrow peak of microcavity fabricated by multiple layers of alternating porosity.

12. The method of claim 11 wherein the luminescent peak is the result of a significant narrowing of the broad luminescence bandwidth of the luminescent sensory material entrapped deep in the semiconductor pores of microcavity.

13. The method of claim 1, wherein said luminescent sensory material entrapped in the semiconductor pores is selected from emissive sensory polymers; emissive sensory molecules or quantum dots; organic emissive molecules or quantum dots blended with non-emissive sensory polymer.

14. The method of claim 1, wherein said semiconductor pores have size in the range of 2-500 nm and made in semiconductor bulk material to provide the light interference for reflected and emissive light.

15. The method of claim 1, wherein porous microcavity or porous monolayer are situated on a top of the bulk semiconductor material and from which they are fabricated.

16. The method of claim 1, wherein porous microcavity or porous monolayer are prepared as a free standing membrane.

17. The method of claim 14, wherein the porous semiconductor is selected from the group consisting of Group II/VI semiconductors, Group III/V semiconductors and Group IV semiconductors.

18. The method of claim 17, wherein the semiconductor is selected from the group consisting of Cds, CdSe, InP, GaAs, Ge, Si and doped Si.

19. The method of claim 1 which provides an enhanced selectivity over the sensor comprising the same luminescent sensory material deposited onto a flat substrate (and do not possessing the narrow luminescent peak) because of multiple intensity monitoring at different detecting wavelengths.

* * * * *